United States Patent
Chen (10) Patent No.: US 8,760,057 B2
(45) Date of Patent: Jun. 24, 2014

(54) FAR INFRARED RAY CERAMIC BULB STRUCTURE

(75) Inventor: Jeong-Shiun Chen, Jiangxi (CN)

(73) Assignee: Jingdezhen Fared Technology Co., Ltd, Jingdezhen, Jiangxi (CN)

( * ) Notice: Subject to any disclaimer, the term of this patent is extended or adjusted under 35 U.S.C. 154(b) by 8 days.

(21) Appl. No.: 13/700,270

(22) PCT Filed: May 21, 2011

(86) PCT No.: PCT/CN2011/074473
§ 371 (c)(1),
(2), (4) Date: Nov. 27, 2012

(87) PCT Pub. No.: WO2011/147287
PCT Pub. Date: Dec. 1, 2011

(65) Prior Publication Data
US 2013/0076243 A1    Mar. 28, 2013

(30) Foreign Application Priority Data
May 28, 2010  (CN) .......................... 2010 1 0185718

(51) Int. Cl.
*H01J 7/24*      (2006.01)
*F21V 9/16*     (2006.01)

(52) U.S. Cl.
USPC .......................................... 315/112; 362/84

(58) Field of Classification Search
None
See application file for complete search history.

(56) References Cited

U.S. PATENT DOCUMENTS

| 8,616,714 | B2* | 12/2013 | Lee et al. ...................... 362/84 |
| 2007/0013998 | A1 | 1/2007 | Wu |
| 2008/0116779 | A1* | 5/2008 | Janson ........................ 313/110 |
| 2012/0262903 | A1* | 10/2012 | Li et al. ......................... 362/84 |
| 2012/0281388 | A1* | 11/2012 | Cai et al. ........................ 362/84 |
| 2012/0293057 | A1* | 11/2012 | Yamamoto et al. ............. 313/45 |

FOREIGN PATENT DOCUMENTS

| CN | 2035534 U | 4/1989 |
| CN | 101390191 A | 3/2009 |
| CN | 101482257 A | 7/2009 |
| CN | 201706273 U | 1/2011 |

\* cited by examiner

*Primary Examiner* — Thienvu Tran
(74) *Attorney, Agent, or Firm* — Muncy, Geissler, Olds & Lowe, P.C.

(57) ABSTRACT

A far infrared ray ceramic bulb structure includes a light emitting element under a ceramic substrate, a far infrared thermal radiation film on the ceramic substrate, a circuit unit, a bulb shell, a bulb shade and a connector connected to an external power supply. The circuit unit in the connector is electrically connected to the light emitting element and the connector. The bulb shade encloses the light emitting element and the ceramic substrate. The bulb shell is connected to the connector and encloses the far infrared thermal radiation film. The far infrared thermal radiation film propagates the heat generated by the light emitting element by far infrared thermal radiation. The working temperature of the light emitting element is reduced and the stability and the efficiency of light emitting are improved to increase the lifetime and the safety.

15 Claims, 6 Drawing Sheets

FAR INFRARED RAY CERAMIC BULB STRUCTURE

BACKGROUND OF THE INVENTION

1. Field of the Invention

The present invention generally relates to a ceramic bulb structure, and more specifically to a far infrared ray ceramic bulb structure having a light emitting element to generate far infrared ray.

2. The Prior Arts

According to studies from many colleges and research institutes around the world, water molecules tends to vibrate at the specific frequency of about 1012/sec when illuminated by far infrared light. Such specifically vibrating water molecules can generate corresponding energy as heat to warm up human tissues, swell the blood vessels and speed up the blood flow so that it is possible for internal tissues to exercise. More specifically, when the water molecules start to vibrate upon being illuminated by far infrared ray, the chemical bond of hydrogen and oxygen in water molecule produces three types of motions, including compression, extension and rotation so as to break the strong hydrogen bonding among individual water molecules in the original larger group of water molecules into smaller group of water molecules, such as a group of 5 or 6 water molecules, which is so-called active water.

In the prior arts, far infrared ray is generally produced by a passive manner, such as printed carbon film, positive thermal coefficient (PTC) heating ceramic or nickel-chromium wire. However, the above method is implemented by heating the far infrared emitter to convert the thermal energy into radiation energy with far infrared spectrum. Therefore, the whole efficiency of energy conversion is low, or specifically much lower than 50%. Additionally, the printed carbon film is configured to generate far infrared ray not greater than 200° C., and the PTC heating ceramic and the nickel-chromium wire can work at the highest temperature of about 250° C. and 300° C., respectively. As a result, the practical application is greatly limited. Besides, the PTC heating ceramic and the nickel-chromium wire in contact with water will cause explosion, and produces serious problems for safety.

Therefore, it is desired to provide a new far infrared ray ceramic bulb structure by using the ceramic substrate, the light emitting element and the far infrared thermal radiation film without any risk of explosion because the far infrared ray ceramic bulb structure is not in contact with water, so as to overcome the above problems in the prior arts.

SUMMARY OF THE INVENTION

Therefore, the present invention has been made in view of the above problems, and it is an objective of the present invention to provide a far infrared ray ceramic bulb structure, which includes a light emitting element formed on the lower surface of a ceramic substrate, a far infrared thermal radiation film formed on the upper surface of the ceramic substrate, a circuit unit, a bulb shell, a bulb shade and a connector connected to an external power supply.

The circuit unit, mounted in the connector, is electrically connected to the light emitting element and the connector. The bulb shade encloses the light emitting element and the ceramic substrate. The bulb shell is connected to the connector and encloses the far infrared thermal radiation film. The far infrared thermal radiation film propagates the heat generated by the light emitting element by far infrared thermal radiation.

Therefore, the working temperature of the light emitting element is reduced and the stability and the efficiency of light emitting are improved to increase the lifetime and the safety.

BRIEF DESCRIPTION OF THE DRAWINGS

The present invention can be understood in more detail by reading the subsequent detailed description in conjunction with the examples and references made to the accompanying drawings, wherein.

DETAILED DESCRIPTION OF THE PREFERRED EMBODIMENTS

The present invention may be embodied in various forms and the details of the preferred embodiments of the present invention will be described in the subsequent content with reference to the accompanying drawings. The drawings (not to scale) show and depict only the preferred embodiments of the invention and shall not be considered as limitations to the scope of the present invention. Modifications of the shape of the present invention shall too be considered to be within the spirit of the present invention.

Figure 1:
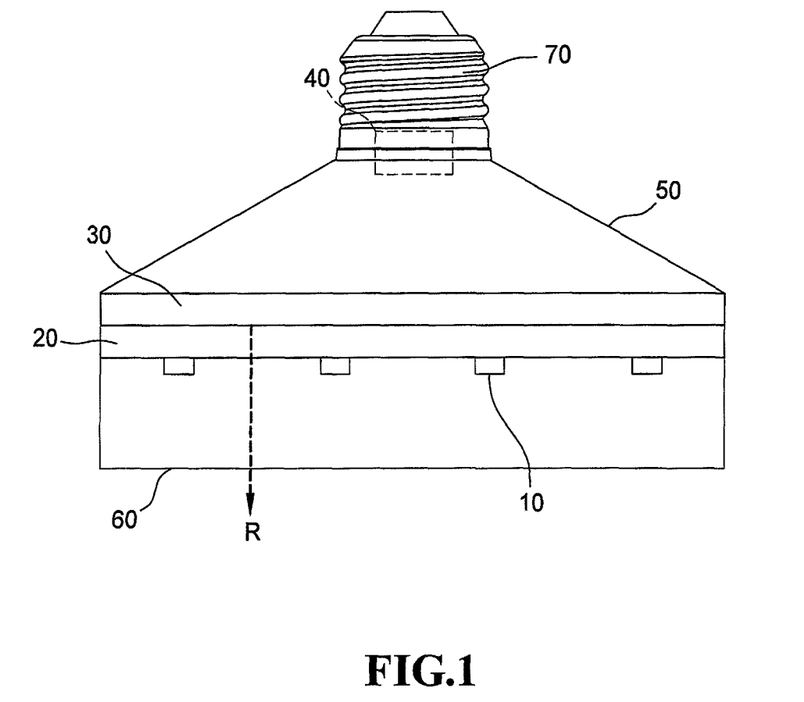
FIG. 1 is a view schematically showing a far infrared ray ceramic bulb structure according to a first embodiment of the present invention.

FIG. 1 clearly illustrates a far infrared ray ceramic bulb structure according to the first embodiment of the present invention, and includes a light emitting element 10, a ceramic substrate 20, a far infrared thermal radiation film 30, a circuit unit 40, a bulb shell 50, a bulb shade 60 and a connector 70. The far infrared ray ceramic bulb structure of the present invention uses the light emitting element 10 to produce light, and the far infrared thermal radiation film 30 to emit far infrared ray R, which has a wavelength primarily within the range of 4 to 400 μm, and especially 6 to 14 μm.

The light emitting element 10 consists of an LED (light emitting diode) chip.

The ceramic substrate 20 has an upper surface and a lower surface. The light emitting element 10 is formed on a sapphire substrate (not shown) and is connected to the lower surface of the ceramic substrate 20. The far infrared thermal radiation film 30 is formed on the upper surface of the ceramic substrate 20. The circuit unit 40 is provided in the connector 70, and the bulb shell 50 is connected to the connector 70 and encloses the far infrared thermal radiation film 30.

The bulb shade 60 encloses the light emitting element 10 and the lower surface of the ceramic substrate 20. The connector 70 connected to an external power source (not shown) is connected to the circuit unit 40 through a first electrical connection line (not shown) to supply electrical power, and furthermore, the circuit unit 40 is connected to the light emitting element 10 through a second electrical connection line (not shown) to transfer electrical signal(s) or supply electrical power used to drive or turn on the light emitting element 10.

The far infrared thermal radiation film 30 consists of a mixture of metal and nonmetal, which consists of at least one of silver, copper, tin, aluminum, titanium and antimony, or at least one alloy of silver, copper, tin, aluminum, titanium and antimony, or at least one of oxide, nitride and inorganic acid of at least one of boron and carbon.

The bulb shell 50 is made from ceramic material or ABS (acrylonitrile butadiene styrene), wherein the ceramic material is suitable for the applications consuming higher power and working at higher temperature, and the ABS material is applicable for medium or lower power and temperature. The bulb shade 60 is made from transparent material, such as polycarbonate or glass.

The far infrared thermal radiation film 30 has a surface microscopic structure, and can propagate the heat generated by the light emitting element 10 and the circuit unit 40 towards the lower surface of the ceramic substrate 20 by thermal radiation R consisting of at least far infrared ray. Because the thermal radiation R generated by the far infrared thermal radiation film 30 consists of far infrared ray, such as the light with the wavelength of 5 µm to 18 µm or preferably 6 µm to 14 µm, the far infrared ray ceramic bulb structure of the first embodiment can generate the far infrared ray as desired.

It should be noted that the connector 70 in FIG. 1 is implemented by a screw type connector, such as E27, for only clearly describing the characteristics of the present invention, and not intended to limit the scope of the present invention. Thus, the connector 70 consists of other types of general connectors, like E14, G4, G9, MR11 or MR16.

Figure 2:
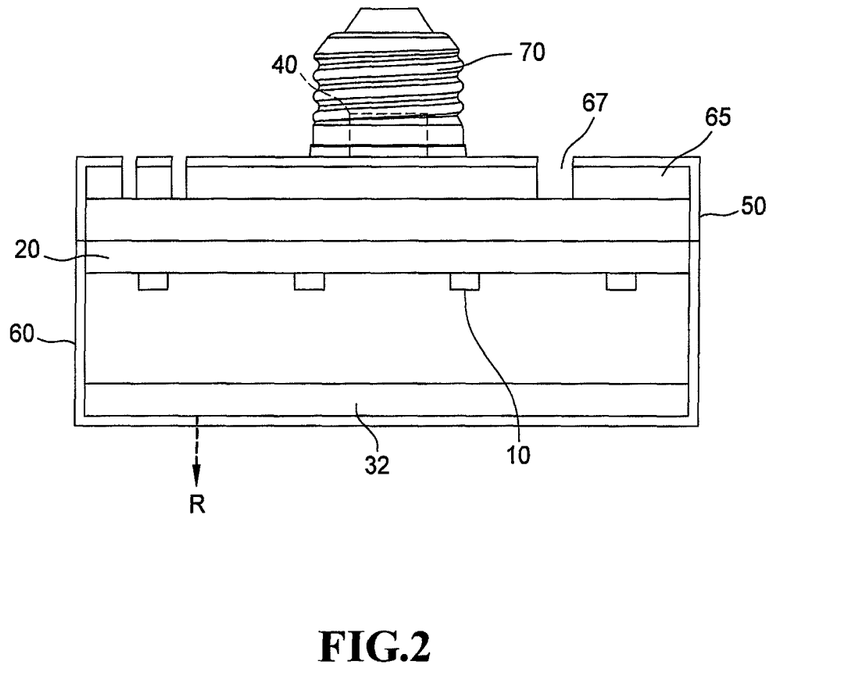
FIG. 2 is a view schematically showing a far infrared ray ceramic bulb structure according to a second embodiment of the present invention.

FIG. 2 illustrates the far infrared ray ceramic bulb structure according to the second embodiment of the present invention. As shown in FIG. 2, the far infrared ray ceramic bulb structure of the present invention includes the LED chip 10, the ceramic substrate 20, the far infrared thermal radiation film 32, the circuit unit 40, the bulb shell 50, the bulb shade 60, the nano-enamel heat dissipation cover 65 and the connector 70. The far infrared ray ceramic bulb structure uses the LED chip 10 to emit light and the far infrared thermal radiation film 32 to generate far infrared ray R.

The far infrared ray ceramic bulb structure in FIG. 2 is similar to the first embodiment of the far infrared ray ceramic bulb structure, and the primary difference is that the far infrared thermal radiation film 32 is formed on the upper surface of the bulb shade 60, that is, the upward surface in FIG. 2.

Another difference is that the bulb shell 50 is connected to the connector 70 and encloses the upper surface of the ceramic substrate 20. Thus, when the light emitted by the LED chip 10 propagates towards the bulb shade 60, the far infrared thermal radiation film 32 on the bulb shade 60 is heated to generate far infrared thermal radiation R direction propagating downwards. Meanwhile, the far infrared thermal radiation film 32 is transparent and allows part of the light emitted by the LED chip 10 to penetrate through and travel downwards so as to provide illumination.

Figure 3:
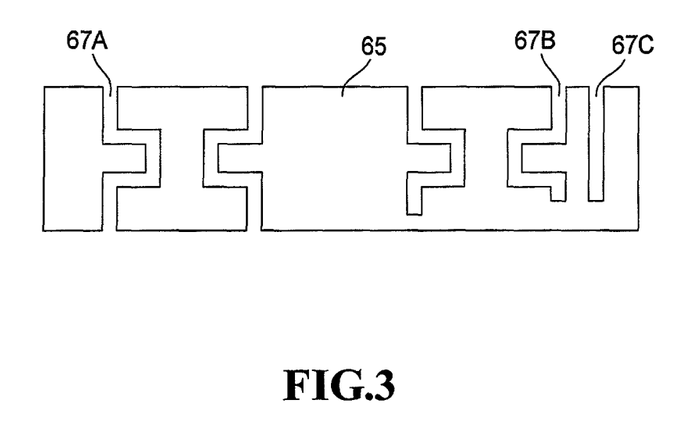
FIG. 3 is a view showing another type of the heat dissipation hole in FIG. 2.

Additionally, a yet another difference is that the nano-enamel heat dissipation cover 65 is provided under the bulb shell 50, and the nano-enamel heat dissipation cover 65 and the bulb shell 50 together enclose the upper surface of the ceramic substrate 20. The nano-enamel heat dissipation cover 65 is formed by sintering nano-particles, and the nano-particles consist of one of aluminum oxide, aluminum nitride, zirconium oxide and calcium fluoride. Additionally, the nano-enamel heat dissipation cover 65 has a plurality of heat dissipation holes 67, and the bulb shell 50 has a plurality of openings corresponding to the heat dissipation holes 67 for enhancing the heat dissipation efficiency by air convention. The nano-enamel heat dissipation cover 65 shown in FIG. 2, is not in contact with the ceramic substrate 20 and separated by a gap. However, it is not intended to limit the scope of the present invention. Alternatively, the nano-enamel heat dissipation cover 65 is in contact with the ceramic substrate 20. The heat dissipation hole 67 has a shape of straight through hole, as shown in FIG. 2, but it is just an illustrative example. Therefore, the heat dissipation hole 67 has any other shape, like the heat dissipation hole 67A with a bent shape, the heat dissipation hole 67B with a bent recess or the heat dissipation hole 67C with a straight recess, as best shown in FIG. 3.

Figure 4:
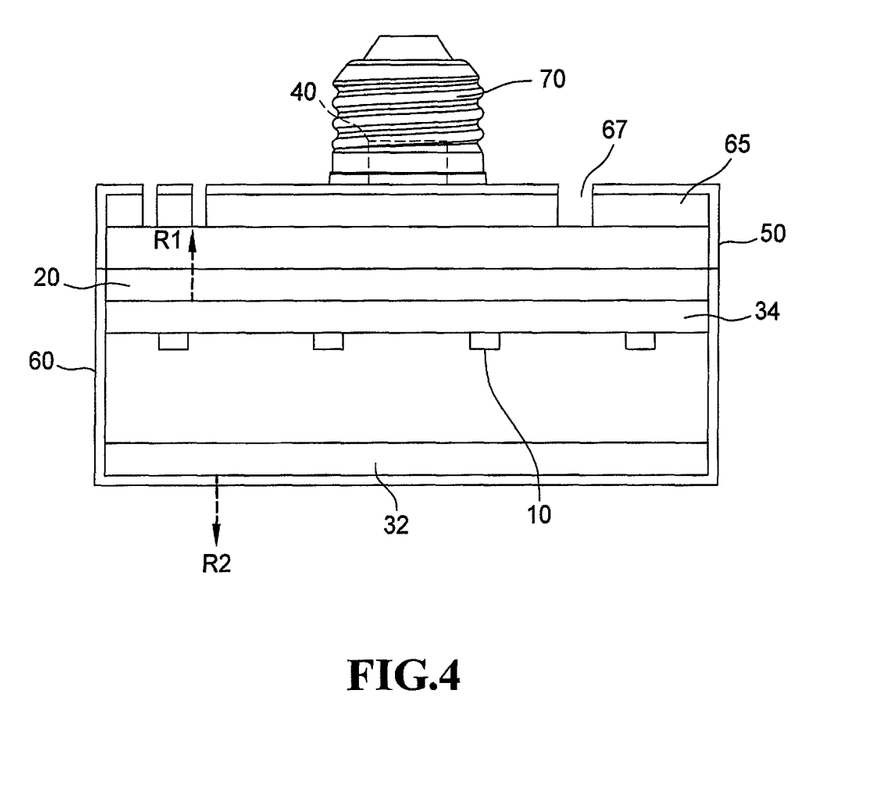
FIG. 4 is a view schematically showing a far infrared ray ceramic bulb structure according to a third embodiment of the present invention.

FIG. 4 illustrates the far infrared ray ceramic bulb structure according to the third embodiment of the present invention. As shown in FIG. 4, the third embodiment of the far infrared ray ceramic bulb structure includes the LED chip 10, the ceramic substrate 20, the far infrared thermal radiation film 32, thermal radiation film 34, the circuit unit 40, the bulb shell 50, the bulb shade 60, the nano-enamel heat dissipation cover 65 and the connector 70. The far infrared ray ceramic bulb structure uses the far infrared thermal radiation film 32 to generate far infrared ray R2 and the thermal radiation film 34 generates far infrared ray R1 so as to further enhance the heat dissipation efficiency.

The far infrared ray ceramic bulb structure in FIG. 4 is similar to the far infrared ray ceramic bulb structure of the second embodiment. That is, the far infrared thermal radiation film 32 in FIG. 4 is similar to the far infrared thermal radiation film 32 in FIG. 2, and the nano-enamel heat dissipation cover 65 in FIG. 4 is similar to the nano-enamel heat dissipation cover 65 in FIG. 2. Thus, the same features are omitted.

The primary difference between the third and second embodiments is that the thermal radiation film 34 of the third and second embodiment is formed on the lower surface of the ceramic substrate 20, and the LED chip 10 is bound to the thermal radiation film 34 by silver paste, wherein the thermal radiation film 34 in FIG. 4 and the far infrared thermal radiation film 32 in FIG. 2 have similar composition. In particular, the thermal radiation film 34 receives the heat generated by the LED chip 10 and propagates the heat by thermal radiation R1 direction towards the nano-enamel heat dissipation cover 65.

Figure 5:
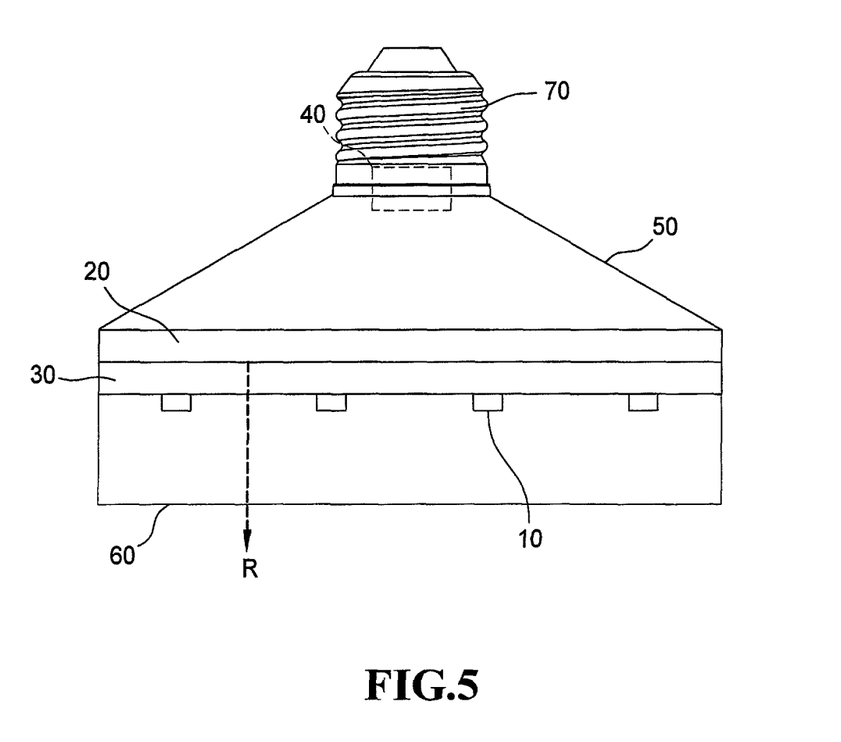
FIG. 5 is a view schematically showing a far infrared ray ceramic bulb structure according to a fourth embodiment of the present invention.

As shown in FIG. 5, the far infrared ray ceramic bulb structure according to the fourth embodiment of the present invention includes the LED chip 10, the ceramic substrate 20, the far infrared thermal radiation film 30, the circuit unit 40, the bulb shell 50, the bulb shade 60 and the connector 70. The far infrared ray ceramic bulb structure uses the LED chip 10 to emit light and the far infrared thermal radiation film 30 generates far infrared ray R with a wavelength within the range of 4 to 400 µm, and especially 6 to 14 µm.

The far infrared ray ceramic bulb structure in FIG. 5 is similar to the far infrared ray ceramic bulb structure of the first embodiment in FIG. 1. The primary difference between the fourth and first embodiments is that the far infrared thermal radiation film 30 of the fourth embodiment is formed under the ceramic substrate 20 and on the LED chip 10, and the heat generated by the circuit unit 40 is directly transferred downwards by far infrared thermal radiation R direction.

Figure 6:
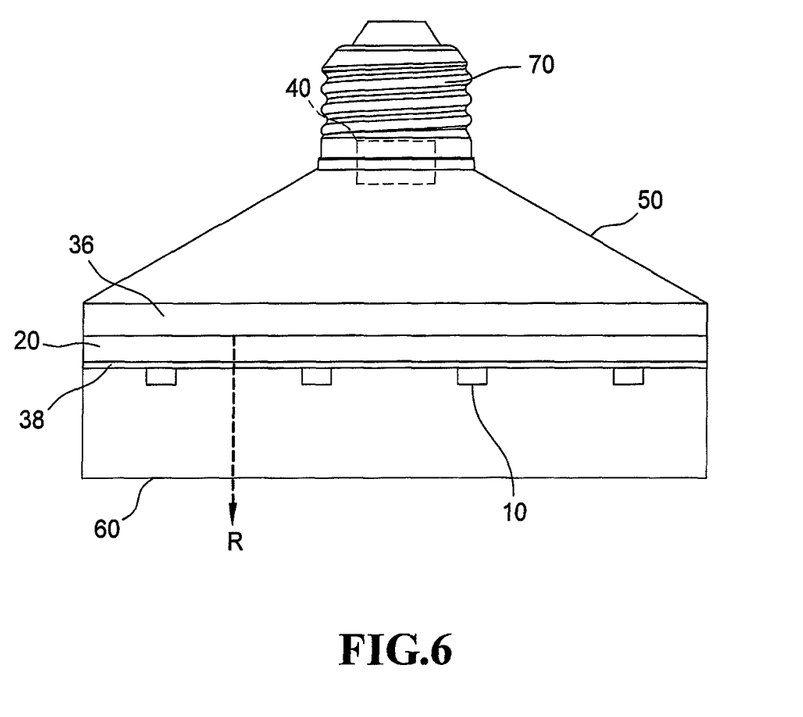
FIG. 6 is a view schematically showing a far infrared ray ceramic bulb structure according to a fifth embodiment of the present invention.

As shown in FIG. 6, the far infrared ray ceramic bulb structure according to the fifth embodiment of the present invention includes the LED chip 10, the ceramic substrate 20, the first far infrared thermal radiation film 36, the second far infrared thermal radiation film 38, the circuit unit 40, the bulb shell 50, the bulb shade 60 and the connector 70. The far infrared ray ceramic bulb structure of the fifth embodiment uses the LED chip 10 to emit light and the second far infrared thermal radiation film 38 generates far infrared ray R with a wavelength within the range of 4 to 400 μm, and especially 6 to 14 μm.

The far infrared ray ceramic bulb structure in FIG. 6 is similar to the far infrared ray ceramic bulb structure of the first embodiment in FIG. 1. The primary difference between the fifth and first embodiments is that the first far infrared thermal radiation film 36 of the fifth embodiment is formed on the ceramic substrate 20, and the second far infrared thermal radiation film 36 is provided under the ceramic substrate 20 and on the LED chip 10 such that the heat generated by the circuit unit 40 is transferred downwards by far infrared thermal radiation R direction.

One aspect of the far infrared ray ceramic bulb structure of the present invention is that the far infrared thermal radiation film receives and absorbs the heat generated by the light emitting element and the circuit unit to generate far infrared ray at normal temperature without additional heating treatment or device so as to avoid any risk due to high temperature process and operation. Therefore, the safety is greatly improved.

Another aspect of the far infrared ray ceramic bulb structure of the present invention is that the far infrared thermal radiation film performs heat dissipation by thermal radiation to reduce the working temperature of the light emitting element, that is, the temperature of the LED chip, such that the problem of the light degradation is solved and the stability of light emitting is enhanced. Thus, the whole efficiency of emitting far infrared ray is considerably increased.

Yet another aspect of the far infrared ray ceramic bulb structure of the present invention is that the nano-enamel heat dissipation cover provides additional effect of heat dissipation. Moreover, the heat dissipation holes of the nano-enamel heat dissipation cover can enhance heat dissipation by air convection. This further reduces the working temperature of the LED chip.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A far infrared ray ceramic bulb structure, comprising:
a ceramic substrate having an upper surface and a lower surface;
a light emitting element formed on a sapphire substrate and connected to the lower surface of the ceramic substrate;
a far infrared thermal radiation film formed on the upper surface of the ceramic substrate, having a surface microscopic structure, and consisting of a mixture of metal and nonmetal;
a circuit unit;
a bulb shell;
a bulb shade enclosing the light emitting element and the lower surface of the ceramic substrate; and
a connector connecting the bulb shell and enclosing the upper surface of the ceramic substrate;
wherein, the connector is connected to an external power source, the circuit unit is provided in the connector, the connector is connected to the circuit unit through a first electrical connection line to supply electrical power, the circuit unit is connected to the light emitting element through a second electrical connection line to transfer electrical signal(s) or supply electrical power used to drive or turn on the light emitting element, and the far infrared thermal radiation film propagates heat generated by the light emitting element and the circuit unit towards the lower surface of the ceramic substrate by thermal radiation consisting of at least far infrared ray.

2. The far infrared ray ceramic bulb structure as claimed in claim 1, wherein the light emitting element consists of an LED chip, the mixture of metal and nonmetal of the far infrared thermal radiation film consisting of at least one of silver, copper, tin, aluminum, titanium and antimony, or at least one alloy of silver, copper, tin, aluminum, titanium and antimony, or at least one of oxide, nitride and inorganic acid of at least one of boron and carbon, and the bulb shell is formed of ceramic material or ABS (Acrylonitrile butadiene styrene).

3. The far infrared ray ceramic bulb structure as claimed in claim 1, wherein the bulb shade is made from polycarbonate or glass.

4. A far infrared ray ceramic bulb structure, comprising:
a ceramic substrate having an upper surface and a lower surface;
a light emitting element formed on a sapphire substrate and connected to the lower surface of the ceramic substrate;
a circuit unit;
a bulb shell having a plurality of openings;
a nano-enamel heat dissipation cover provided under the bulb shell;
wherein, the nano-enamel heat dissipation cover and the bulb shell together enclose the upper surface of the ceramic substrate and the circuit unit, the nano-enamel heat dissipation cover has a plurality of heat dissipation holes corresponding to the openings in the bulb shell, and the nano-enamel heat dissipation cover is or not in contact with the ceramic substrate;
a bulb shade enclosing the light emitting element and the lower surface of the ceramic substrate;
a far infrared thermal radiation film formed on the upper surface of the ceramic substrate facing the light emitting element, having a surface microscopic structure, and consisting of a mixture of metal and nonmetal, wherein the far infrared thermal radiation film allows at least part of the light emitted by the light emitting element to penetrate therethrough; and
a connector connecting the bulb shell and enclosing the upper surface of the ceramic substrate;
wherein the connector is connected to an external power source, the circuit unit is provided in the connector, the connector is connected to the circuit unit through a first electrical connection line to supply electrical power, the circuit unit is connected to the light emitting element through a second electrical connection line to transfer electrical signal(s) or supply electrical power used to drive or turn on the light emitting element, and the far infrared thermal radiation film generates thermal radiation consisting of at least far infrared ray, which propagates towards a lower surface of the bulb shade.

5. The far infrared ray ceramic bulb structure as claimed in claim 4, wherein the light emitting element consists of an LED chip, and the mixture of metal and nonmetal of the far infrared thermal radiation film consisting of at least one of silver, copper, tin, aluminum, titanium and antimony, or at least one alloy of silver, copper, tin, aluminum, titanium and antimony, or at least one of oxide, nitride and inorganic acid of at least one of boron and carbon.

6. The far infrared ray ceramic bulb structure as claimed in claim 4, wherein the heat dissipation holes consists of at least one of a straight through hole, a bent through hole, a straight recess and a bent recess.

7. The far infrared ray ceramic bulb structure as claimed in claim 4, wherein the bulb shade is made from polycarbonate or glass.

8. A far infrared ray ceramic bulb structure, comprising:
a ceramic substrate having an upper surface and a lower surface;
a thermal radiation film formed on the lower surface of the ceramic substrate, having a surface microscopic structure, and consisting of a mixture of metal and nonmetal;
a circuit unit;
a light emitting element formed on a sapphire substrate and bound to the far infrared thermal radiation film by sliver paste;
a bulb shell having a plurality of openings;
a nano-enamel heat dissipation cover provided under the bulb shell;
wherein the nano-enamel heat dissipation cover and the bulb shell together enclose the upper surface of the ceramic substrate and the circuit unit, the nano-enamel heat dissipation cover has a plurality of heat dissipation holes corresponding to the openings of the bulb shell, and the nano-enamel heat dissipation cover is or not in contact with the ceramic substrate;
a bulb shade;
a far infrared thermal radiation film formed on the upper surface of the bulb shade facing the light emitting element, having a surface microscopic structure and consisting of a mixture of metal and nonmetal, wherein the far infrared thermal radiation film allows at least part of the light emitted by the light emitting element to penetrate; and
a connector connecting the bulb shell and enclosing the upper surface of the ceramic substrate;
wherein, the connector is connected to an external power source, the circuit unit is provided in the connector, the connector is connected to the circuit unit through a first electrical connection line to supply electrical power, the circuit unit is connected to the light emitting element through a second electrical connection line to transfer electrical signal(s) or supply electrical power used to drive or turn on the light emitting element, the thermal radiation film propagates heat towards the nano-enamel heat dissipation cover by thermal radiation, and the far infrared thermal radiation film generates thermal radiation consisting of at least far infrared ray and propagating towards a lower surface of the bulb shade.

9. The far infrared ray ceramic bulb structure as claimed in claim 8, wherein the light emitting element consists of an LED chip, and the mixture of metal and nonmetal of each of the thermal radiation film and the far infrared thermal radiation film consisting of at least one of silver, copper, tin, aluminum, titanium and antimony, or at least one alloy of silver, copper, tin, aluminum, titanium and antimony, or at least one of oxide, nitride and inorganic acid of at least one of boron and carbon.

10. The far infrared ray ceramic bulb structure as claimed in claim 8, wherein the heat dissipation holes consists of at least one of a straight through hole, a bent through hole, a straight recess and a bent recess.

11. The far infrared ray ceramic bulb structure as claimed in claim 8, wherein the bulb shade is made from polycarbonate or glass.

12. A far infrared ray ceramic bulb structure, comprising:
a ceramic substrate having an upper surface and a lower surface;
a light emitting element formed on a sapphire substrate and connected to the lower surface of the ceramic substrate;
a far infrared thermal radiation film formed between the lower surface of the ceramic substrate and the light emitting element, having a surface microscopic structure, and comprising a mixture of metal and nonmetal;
a circuit unit;
a bulb shell;
a bulb shade enclosing the light emitting element and the lower surface of the ceramic substrate; and
a connector connecting the bulb shell and enclosing the upper surface of the ceramic substrate;
wherein, the connector is connected to an external power source, the circuit unit is provided in the connector, the connector is connected to the circuit unit through a first electrical connection line to supply electrical power, the circuit unit is connected to the light emitting element through a second electrical connection line to transfer electrical signal(s) or supply electrical power used to drive or turn on the light emitting element, and the far infrared thermal radiation film propagates heat generated by the light emitting element and the circuit unit downwards by far infrared thermal radiation.

13. The far infrared ray ceramic bulb structure as claimed in claim 12, wherein the light emitting element consists of an LED chip, and the mixture of metal and nonmetal of the far infrared thermal radiation film consisting of at least one of silver, copper, tin, aluminum, titanium and antimony, or at least one alloy of silver, copper, tin, aluminum, titanium and antimony, or at least one of oxide, nitride and inorganic acid of at least one of boron and carbon, and the bulb shell is formed of ceramic material or ABS.

14. A far infrared ray ceramic bulb structure, comprising:
a ceramic substrate having an upper surface and a lower surface;
a light emitting element formed on a sapphire substrate and connected to the lower surface of the ceramic substrate;
a first thermal radiation film formed on the upper surface of the ceramic substrate;
a second thermal radiation film formed between the lower surface of the ceramic substrate and the light emitting element;
a circuit unit;
a bulb shell;
a bulb shade enclosing the light emitting element and the lower surface of the ceramic substrate; and
a connector connecting the bulb shell and enclosing the upper surface of the ceramic substrate;
wherein, the connector is connected to an external power source, the circuit unit is provided in the connector, each of the first thermal radiation film and the second thermal radiation film comprises a mixture of metal and nonmetal and has a surface microscopic structure, the circuit unit is provided in the connector, the connector is connected to the circuit unit through a first electrical connection line to supply electrical power, the circuit unit is connected to the light emitting element through a second electrical connection line to transfer electrical signal(s) or supply electrical power used to drive or turn on the light emitting element, and the first thermal radiation film and the second thermal radiation film propagate heat generated by the light emitting element and the circuit unit downwards by far infrared thermal radiation.

15. The far infrared ray ceramic bulb structure as claimed in claim 14, wherein the light emitting element consists of an LED chip, and the mixture of metal and nonmetal of each of the first thermal radiation film and the second thermal radiation film consisting of at least one of silver, copper, tin, aluminum, titanium and antimony, or at least one alloy of silver, copper, tin, aluminum, titanium and antimony, or at least one of oxide, nitride and inorganic acid of at least one of boron and carbon, and the bulb shell is formed of ceramic material or ABS.

* * * * *